United States Patent [19]

Muhler et al.

[11] 4,042,680

[45] Aug. 16, 1977

[54] ANTICARIOGENIC MALOALUMINATE COMPLEXES

[75] Inventors: Joseph C. Muhler, Howe; Mark S. Putt; Carl J. Kleber, both of Forth Wayne, Ind.; Clayton W. Yoho, Racine, Wis.

[73] Assignee: Indiana University Foundation, Bloomington, Ind.

[21] Appl. No.: 710,443

[22] Filed: Aug. 2, 1975

[51] Int. Cl.² ............................................... A61K 7/24
[52] U.S. Cl. ................................... 424/55; 260/448 R
[58] Field of Search ....................... 260/448 R; 424/55

[56] References Cited

U.S. PATENT DOCUMENTS 3,485,858  12/1969  Gee et al. .......................... 260/448 R
3,584,025  6/1971  Boye et al. ........................ 260/448 R

*Primary Examiner*—Lewis Gotts
*Assistant Examiner*—Cary Owens
*Attorney, Agent, or Firm*—Kirkland & Ellis

[57] ABSTRACT

Aqueous anionic maloaluminate complexes of the structure:

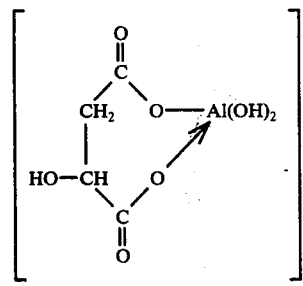

at mildly alkaline pH are effective in reducing the incidence and severity of dental caries. These complexes may be advantageously incorporated in aqueous oral compositions, especially dentifrices, having pH values lying in the range of about 7.0 - 9.0.

8 Claims, No Drawings

ANTICARIOGENIC MALOALUMINATE COMPLEXES

BACKGROUND OF THE INVENTION

1. Field of the Invention

The present invention relates to new maloaluminate compositions of matter and to oral compositions containing such materials that are effective in reducing the incidence and severity of dental caries.

2. Description of the Prior Art

It is commonly recognized that the presence of small amount of fluoride occurring naturally in drinking water (e.g., 1.0 microgram fluoride per milliliter) has a pronounced effect in reducing the incidence of dental caries in permanent teeth of children consuming such water from birth through eight years of age. Fluoride salts have been introduced into public water supplies in many communities with similar results. This method of dental caries prophylaxis is not available, however, to large numbers of people whose drinking water is obtained from small, private, fluoride-deficient sources such as individual wells and the like. Further, the addition of fluoride to common public water sources is not always accepted or permitted.

Topical application of aqueous fluoride solutions by dentists or dental hygienists likewise provides an excellent measure of protection against dental caries. Various fluoride compounds have been employed in this manner, including stannous fluoride and sodium fluoride. Another method of employing the anticariogenic properties of fluoride salts comprises incorporating such materials with a compatible abrasive to form a prophylactic past composition for use by dentists or dental hygienists on a professional basis.

Limitations on the availability of fluoride therapy by way of water supply or professional treatment has led to extensive efforts to incorporate fluoride salts in oral compositionsfor use in the home in the form of fluoride-containing dentifrices. Although effective dental caries protection has been obtained through the use of the aforementioned fluoride-containing compounds, occasional side effects havebeen experienced with certain of the known fluoride-containing anticariogenic agents, particularly certain tin-containing salts. For example, a brownish pigmentation of carious or precarious lesions has been experienced after anticariogenic agents containing the stannous ion have been applied to the teeth when the teeth are not properly cleaned with a toothbrush. Although the stain is not necessarily undesirable from a physiological standpoint, nevertheless, for aesthetic reasons it would be desirable to provide an effective anticariogenic agent that does not pigment carious enamel.

The utility of certain of the prior art anticariogenic fluoride materials has also been limited by the extent of their solubility in aqueous media. For example, sodium fluoride is only soluble to the extent of about 4% in water.

Furthermore, because of the concern from a toxicity standpoint, current regulations imposed by the U.S. Food and Drug Administration limit the amount of fluoride that can be provided in products sold for over-the-counter use.

Finally, certain of the known prior art anticariogenic agents have been relatively unstable in aqueous solution. For example, stannous fluoride is subject to both oxidation and hydrolysis and for that reason must be used in freshly prepared form and must be used in conjunction with complexing anions in order to obtain its optimal anticariogenic effect.

For the foregoing and other reasons, dental researchers have continued their efforts to develop new, non-fluoride anticariogenic agents which demonstrate a high level of anticariogenic effectiveness as compared to fluorides but which are non-toxic, stable, and widely available. It has been suggested that aluminum salts may have a beneficial effect in reducing dental caries itself or in facilitating the uptake of fluoride by the dental enamel. See, e.g., Manly et al., "Substances Capable of Decreasing the Acid Solubility of Tooth Enamel", J. Den. Res. 28: 160 (1948); Regolati, et al., "Effects of Aluminum and Fluoride and Caries, Fluorine Content and Dissolution of Rat Molars", Hel. Odont. Acta. 13: 59 (1969); and Kelada, "Electrochemical Characteristics of Free and Complexed Fluorides in Drinking Water and The Effects of Aluminum and Iron on Fluoride Incorporation Into Tooth Enamel, Univ. Michigan Thesis (1972).

In vitro studies have shown that pretreatment of enamel with aluminum solutions resulted in increased fluoride uptake when followed by treatment with a fluoride solution; however, treatment with combinations of aluminum and fluoride did not afford any added benefit over that of fluoride alone. McCann, "The Effect of Fluoride Complex Formation of Fluoride Uptake and Retention in Human Enamel", Archs. Oral Biol. 14:521 (1969); and Gerhardt, et al., "Fluoride Uptake in Natural Tooth Surfaces Pretreated with Aluminum Nitrate", J. Dent. Res. 51:870 (1972). Moreover, the foregoing techniques have dealt primarily with the use of aluminum in combination with fluorides in acidic media and have not focussed on the effect of aluminum in the absence of fluoride and in alkaline media.

Thus, while some elements are known to inhibit dental caries (e.g., F, Mo., Sr, and V) and while others are known to promote dental caries (e.g., Se, Mg, and Cd), the preponderance of data on aluminum indicate that it is dental caries inert as classified by Navia, "Effect of Minerals on Dental Caries", in *Dietary Chemicals vs. Dental Caries,* A.C.S., Washington, D.C. (1970).

Nor has the use of aluminum salts in dentifrices demonstrated the desired result, primarily because they have failed to recognize that conventional dentifrice constituents such as abrasives are incompatible with sources of biologically available aluminum. Thus, while French Pat. No. 3610M describes a specific combination of aluminum lactate, aluminum fluoride and calcium pyrophosphate, the abrasive interferes with the aluminum by reacting therewith to form insoluble aluminum phosphate, Similarly, U.S. Pat. No. 3,195,356 uses aluminum salts such as aluminum fluoride to coact with insoluble sodium metaphosphate abrasives to reduce the solubility of such abrasives and to increase fluoride uptake, but without independent therapeutic advantage being taken of the aluminum.

U.S. Pat. No. 3,282,792 describes low pH stannous fluoride dentifrices stabilized against precipitation and oxidation of stannous tin ions through the use of hydroxyl substituted de- and tri-carboxylic acids. However, nothing is said in the patent regarding the use of aluminum with respect to anticariogenic systems that do not contain fluoride. Similarly, while U.S. Pat. No. 3,937,806 teaches oral compositions comprising indium and fluoride to which malic acid is added to stabilize the indium, the patent does not recognize that beneficial results may be achieved with aluminum and carboxylic acids without incorporating fluoride.

Canadian Patent No. 928,272 describes acidic dentifrices comprising a combination of surface active substances and albumencoagulating substances such as certain carboxylic acid salts of aluminum and othe metals. However, this patent likewise fails to teach that significant dental health benefits can be achieved with alkaline aluminum systems. And while the reaction of aluminum chloride and ammonium malate in varying ratios at different pH's has been studied (Kalalova, "Disintegration of Compounds of Aluminum with Malate-Anion Through Warming", Scientific Papers of the Institute of Chem. Tech. Prague B(17) 1973 Inorganic Chem, and Tech. p. 167), the author failed to isolate a stable aqueous maloaluminate complex existing at pH greater than 7.0 and less than 9.0 nor is any suggestion made as to possible dental utility of such material in oral compositions.

Thus, the prior art has as yet not developed a stable alkaline system providing biologically available aluminum in anticariogenic oral compositions.

Accordingly, it is a primary object of the present invention to provide a new composition of matter effective in reducing the incidence and severity of dental caries.

A related object is to provide new anticariogenically effective non-fluoride oral compositions.

Another object is to provide new maloaluminate complexes which are effective in weakly alkaline oral compositions.

SUMMARY OF THE INVENTION

The foregoing and other objects, advantages, and features of the present invention may be achieved with mildly alkaline (pH7.0 – 9.0) aqueous anionic maloaluminate complexes of the structure:

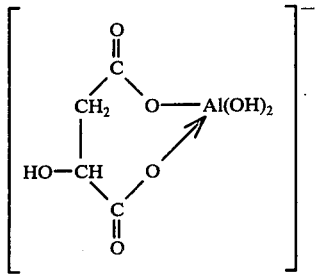

Weakly alkaline (pH more than about 7.0 and less than about 9.0) aqueous oral compositions incorporating such compositions have been shown to be effective in oral compositions in reducing the incidence and severity of dental caries.

The foregoing maloaluminate complexes may be provided in combination with carries suitable for use in the oral cavity. Such carriers include, in the cases of dentifrices and prophylaxis pastes, cleaning and polishing agents and other constituents of such compositions. In the case of topical solutions and mouthwashes, suitable carriers include water and other liquids. Indeed, substantially any aqueous carrier capable of supplying the active agent to the oral hard tissues may beemployed in accordance with this invention.

The maloaluminate complexes of this invention are provided in oral compositions at the level 0.007 – 35.7%, by weight, preferably about 0.07 – 3.6%, by weight.

PREPARATION AND PROPERTIES

The aqueous anionic maloaluminate complexes of this invention may be prepared by a variety of methods so long as aluminum ions and malate ions are provided in an aqueous medium at a pH in the range of about 7.0 up to about 9.0 in malate to aluminum ion ratio of at least 1:1. The foregoing pH range is believed to be critical in the sense that the complex of the following desired structure appears to be found only in this pH range:

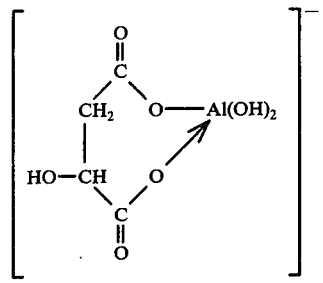

The aluminum ions may be supplied by substantially any water-soluble aluminum salt such as aluminum potassiumsulfate, $AlK(SO_4)_2.12H_2O$; aluminum chloride, $AlCl_3.6H_2O$; aluminum sodium sulfate, $AlNa(SO_4)_2.12H_2O$; aluminum ammonium sulfate, $AlNH_4(SO_4)_2.12H_2O$; aluminum sodium phosphate, $NaAl_3H_{14}(PO_4)_8.4H_2O$; aluminum sulfate, $Al_2(SO_4)_3.16H_2O$; aluminum nitrate, $Al(NO_3)_3.9H_2O$; and sodium aluminate, $NaAl(OH)_4$.

The malate anion may be supplied as malic acid or as substantially any nontixic, water-soluble malate salt such as sodium malate, potassium malate, ammonium malate, and mixtures thereof.

The malate anion and aluminum ion are optimally supplied in a molar ratio of about 1:1. However, the benefits of this invention may be obtained at malate to aluminum ionic molar ratios lying generally in the range of about 1:1 to about 6:1.

The anionic maloaluminate complex may be formed by supplying aluminum and malate ions at the indicated levels in an aqueous medium at pH lying in the range of greater than about 7.0 and less than about 9.0. Formation of the complex appears to be optimal at a pH of about 8.0. Alternatively, the desired complexes may be formed in situ during the formulation of oral compositions produced in accordance with this invention.

While as noted, the complexes may be prepared by supplying the aluminum ions and malic acid, it is desirable to prepare the complexes and to exclude the presence of spectator ions (such as chloride ions present where the aluminum is supplied as aluminum chloride) which could adversely affect taste (e.g., by entraining sodium chloride in the compositions).

Suitable preparation routes which may be used to avoid the presence of such spectator ions include reacting sodium aluminate and malic acid in an aqueous medium at the proper pH so as to form the complex directly. Another method is to react aluminum sulfate and malic acid and thereafter to remove the sulfate ion by adding barium hydroxide so as simultaneously to precipitate spectator ions and adjust the pH. A still further method involves passing a solution containing spectator ions over a mixed-bed ion exchange column in order to obtain a spectator ion-free system.

A variety of other procedures may be employed as will be obvious to those skilled in the art. Exemplary methods of preparing the maloaluminate complexes of this invention are given in the following examples.

EXAMPLE I

Sodium aluminate was prepared by dissolving 837.24 grams (20.93 moles) of sodium hydroxide pellets in 1,000.00 grams of water in a 3 necked, 3 liter reaction flask fitted with a vented condenser to prevent water loss during digestion of the alumina. A ground glass stirring rod was introduced through one of the necks of the flask which was heated by a heating mantle to bring th caustic solution to a slow boil. Stirring was continued, and ten to twenty grams of alumina at a time was added and allowed to dissolve before more is added. A total of 1,216.48 grams(15.50 moles) of alumina were added in this manner. The resulting syrupy sodium aluminate solution was then allowed to cool to room temperature, and water lost by evaporation was replaced.

In a 2 liter volumetric flask containing 1,800 ml of deionized water 10.00 grams (0.0037 moles/liter) malic acid were dissolved. While stirring the malic acid solution vigorously, 14.71 grams (0.0037 moles/liter) of sodium aluminate solution prepared in the foregoing manner was added dropwise. A final dilution to 2,000 ml was made with water. The unadjusted pH of this solution was 7.8, immediately after preparation. Before final dilution is made, the pH can be adjusted with NaOH or Hcl.

EXAMPLE IA

One hundred milliters of deionized water and 26.8 grams of malic acid were added to a 3 necked, 250 ml round bottom reaction flask fitted with a distribution apparatus, a heating mantle and a magnetic stirrer. The mixture was stirred to dissolve the malic acid and was brought to a gentle boil. Aluminum isopropoxide (20.7 grams) was added incrementally to the acid solution with liberation of isopropanol. When all of the isopropanol had been azeotrooped out of the mixture, the remaining to bring the solution weight to 77.64 grams (3.48% aluminum). Twenty-five grams of the solution were added with stirring to a 2 liter beaker containing 1638.08 grams of water. Sodium aluminate (5.92 grams) as prepared in Example I was slowly added to yield a solution containing 1050 ppm aluminum at pH 4.9. The pH was then adjusted to the 7.0-9.0 range by the addition of sodium hydroxide.

EXAMPLE II $CO_2$ free deionized water (94.63 parts by weight) was placed in a glass beaker on a magnetic stirring apparatus. Dry nitrogen gas was passed over the liquid surface, and aluminum sulfate hexadecylhydrate (3.76 parts by weight) was then added and mixed thoroughly. Malic acid (1.61 parts by weight) was then added and the solution was mixed until clear. The resulting solution was stored in a glass container under a nitrogen atmosphere. Fifty grams of the foregoing solution (0.00596 mole saluminum ion, 0.006 moles malic acid) and 69.5 grams of 4% barium hydroxide octahydrate solution (.0088 moles barium ion) were separately to near boiling, and were rapidly mixed with stirring. Exactly 3.4g. of a 10% sodium hydroxide solution (0.0055 moles NaOH) were then added with continued stirring, and the resulting mixture was digested for two hours near its boiling point. The mixture was allowed to cool to room temperature and water lost was added back with stirring. The mixture was allowed to sit for six days at room temperature, the clear supernatant was decanted off into a 5 Whatman paper gravity filter apparatus, and the clear filtrate was recovered. After five days storage the resulting solution had a pH of 7.55.

EXAMPLE III

Redistilled water (950 mls) was placed in a 1 liter glass beaker, and 1.7986g of $AlCl_3.6H_2O$ was dissolved in the water followed by the addition of 1.000g of malic acid. The pH of the resultant solution was adjusted to 7.9±0.1 by the dropwise addition of concentrated NaOH with constant stirring. After pH adjustment the solution was quantitatively transferred to a 1 liter volumetric and filled to the mark.

The resulting solutions from Examples I-III were evaporated under vacuum at a temperature of about 50° C. in a rotary evaporation to a concentration of 5.3% by weight aluminum, and these solutions were used in formulating oral compositions in accordance with this invention.

The following structure of the maloaluminate complex anion has been verified by nuclear magnetic resonance ("NMR") spectroscopy.

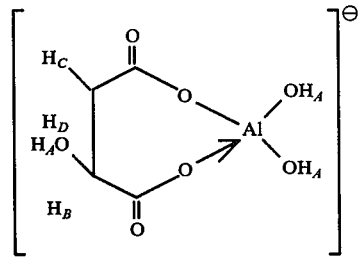

The structure of aluminum malate is derived from the study of relative molar quantities of aluminum chloride, malic acid and sodium deuteroxide in relation to the observed and continuous changes in acidity (pH) an proton magnetic resonance spectra during the controlled sequences of reactions. The proton magnetic resonance spectra were taken by the Varian NMR machine, HA60, in deuterium oxide with sodium salt of 3-(Tri-methyl-silyl)-1-propanesulfonic acid as reference standard. AT pH 8, the structure has proton magnetic resonance absorptions at 287, 259.5, 115.5 and 110.4 cycles/second for the respective protons of A, B, C and D. The absorption of protons A is a singlet. The absorption of proton B is a broad quartet while the absorptions of protons C and D are two sets of quartets which are superimposed on each other as a broad multiplet.

ORAL COMPOSITIONS COMPRISING MALOALUMINATE COMPLEXES

The maloaluminate complexes of this invention have demonstrated significant utility as anticariogenic agents for use in oral compositions comprising carriers such as abrasives, water, and other non-toxic materials. The compositions of this invention may be applied to the teeth in aqueous solution form (such as in a topical treatment solution or in the form of an aqueous mouthwash). However, they are also well suited for other oral compositions for dental caries prophylaxis (e.g., dentifrices and prophylaxis pastes) which contain one or more ionically compatible carries such as an abrasive.

In general, the oral compositions produced in accordance with the present invention comprise from about 0.007 to about 35.7%, by weight, of the maloaluminate complex, preferably about 0.07% - 3.6%, by weight, calculated as maloaluminate anion.

DENTIFRICE PREPARATIONS

Oral compositions adapted for regular home use such as dentrifrice preparations and the like typically comprise about 10-95%, by weight, of compatible cleaning and polishing agents as a carrier suitable for use in the oral cavity.

Various compatible cleaning and polishing agents, suitable for use in dentifrice preparations include purified, calcined kaolin abrasives disclosed in a co-pending application of Joseph C. Muhler, et al entitled "DENTRIFRICE PREPARATIONS COMPRISING PURIFIED, CALCINED KAOLIN ABRASIVES", Ser. No. 710444, filed herewith; calcined aluminum silicate abrasives of the type described in U.S. Pat. No. 3,105,013, commercially available under the trademark "Kaopolite SF"; zirconium silicate as described and claimed in U.S. Pat. No. 3,450,813; and calcined and uncalcined talcs, $Mg_3Si_4O_{10}(OH)_2$ and barium sulfate. Mixtures of such abrasives may also be employed. Preferably, purified, calcined kaolin abrasives are employed in such dentifrice preparations.

Dentifrice preparations in accordance with the subject invention are prepared in a conventional manner and usually include additional ingredients which render the over-all compositions commercially acceptable to consumers.

Thus, toothpastes require a binder substance to impart desired textural properties. Alkoxylated cellulose derivatives, nonionic agents resulting from the addition of ethylene oxide to condensation products of propylene oxide and propylene glycol, natural gum binders such as gum tragancanth, gum karaya, gum arabic, gum xanthan, etc., and seaweed derivatives such as Irish moss and alginates and water-soluble cellulose derivatives, such as sodium carboxymethyl cellulose can be used for this purpose. Synthetic colloidal magnesium silicate, such as "Laponite", also may be used and is preferred in gel-type formulations. Desirably, those materials were employed which are most compatible with aluminum ions. Improvements in texture can also be attained by including an additional material such as colloidal magnesium aluminum silicate or colloidal silica. Binders in an amount of from 0.5%, by weight, can be used to form a satisfactory toothpaste.

Toothpastes conventionally contain sudsing agents. Suitable sudsing agents include, but are not limited to, water-soluble alkyl sulfates having from 8 to 18 carbon atoms in the alkyl radical, such as sodium lauryl sulfate, ethyoxylated fatty ethers or ethyoxlated fatty alcohol esters, water-soluble salts of sulfonated monoglycerides of fatty acids having from 10 to 18 carbon atoms in the alkyl radical such as sodium coconut monoglyceride sulfonate, salts of fatty acid amides of taurines such as sodium-N-methyl palmitoyl taurine, anionic surfactants, and salts of fatty acid esters of isethionic acid. Sudsing agents can be used in the compositions of this invention in an amount of from about 0.5% to about 5.0%, by weight, of the total composition.

It is also desirable to include some humectant material in a toothpaste to keep it from hardening. Materials commonly used for this purpose include glycerine, sorbitol, and other polyhydric alcohols. The humectants can comprise up to 35% of conventional toothpaste compositions. In the case of gel-type formulations, humectants may be used at levels as high as 80%, by weight, Finally, flavoring materials may be included in a toothpaste formulation including small amounts of oils of wintergreen and peppermint and sweetening agents such as saccharin, dextrose, and levulose.

Compositions of dentifrices employing the complexes of this invention are given in the following Examples.

EXAMPLE IV

| Constituent | Parts by Weight |
|---|---|
| Maloaluminate complex (Example I) | 3.78 |
| Purified, calcined kaolin | 37.00 |
| Water | 21.05 |
| Sorbitol | 17.50 |
| Glycerine | 14.00 |
| Sodium lauryl sulfate | 1.50 |
| Fumed silica | 2.00 |
| Xanthan gum | 1.50 |
| Flavorings, coloring etc. | 1.46 |
| Sodium hydroxide (50%) | .21 |
| | 100.00 |

EXAMPLE V

| Constituent | Parts by weight |
|---|---|
| Maloluminate complex (Example II) | 3.78 |
| Calcined aluminum silicate | 37.00 |
| Water | 17.27 |
| Sorbitol | 17.50 |
| Glycerine | 14.00 |
| Sodium lauryl sulfate | 1.50 |
| Fumed silica | 2.00 |
| Xanthan Gum | 1.50 |
| Flavoring, colorings, preservatives, etc. | 1.46 |
| Sodium hydroxide (50%) | 0.21 |
| | 100.00 |

EXAMPLE VI

| Constituent | Parts by Weight |
|---|---|
| Maloaluminate complex (Example III) | 7.56 |
| Zirconium silicate | 37.00 |
| Water | 17.27 |
| Sorbitol | 17.50 |
| Glycerine | 14.00 |
| Sodium lauryl sulfate | 1.50 |
| Fumed silica | 2.00 |
| Xanthan gum | 1.50 |
| Flavorings, colorings, preservatives | 1.46 |
| Sodium hydroxide (50%) | 0.21 |
| | 100.00 |

EXAMPLE VII

| Constituent | Parts by Weight |
|---|---|
| Aluminum chloride | 0.89 |
| Malic acid | 0.50 |
| Purified, calcined kaolin | 27.00 |
| Water | 22.16 |
| Sorbitol | 17.50 |
| Glycerine | 14.00 |
| Sodium lauryl sulfate | 1.50 |
| Fumed silica | 2.00 |
| Xanthan gum | 1.50 |
| Preservatives, flavors, etc. | 1.46 |
| Sodium hydroxide | 1.49 |
| | 100.00 |

A formulation of a suitable gel-type dentifrice is given in Example VIII.

EXAMPLE VIII

| Constituent | Parts by Weight |
|---|---|
| Maloaluminate complex (Example I) | 7.56 |
| Precipitated silica | 22.00 |
| Sorbitol | 60.54 |
| Glycerine | 4.50 |
| Sodium lauryl sulfate | 1.50 |
| Synthetic sodium magnesium silicate | 1.00 |
| Sodium carboxymethyl cellulose | .20 |
| Sodium hydroxide (50%) | .70 |
| Flavorings, etc. | 2.00 |

-continued

| | 100.00 |

PROPHYLACTIC PASTE COMPOSITIONS

Oral compositions of the present invention include, in addition to the described dentifrice preparations, prophylactic paste compositions adapted for relatively infrequent application (e.g., once or twice a year), either professionally (i.e., by a dentist or dental hygienist) or by self-application under professional supervision. A prophylactic paste composition generally differs from a dentifrice composition in that the cleaning and polishing component thereof is more abrasive (and as a result, is a better tooth cleaner). Since a prophylactic paste composition is applied only once or twice per year, a more abrasive cleaning and polishing agent may safely be employed therein than in a dentifrice preparation (i.e., if the more abrasive cleaning and polishing agent were used in a dentifrice preparation adapted for frequent application, the agent might permanently damage the oral hard tissues).

The compatible substances previously described as suitable cleaning and polishing agents for incorporation in dentifrice preparations may also be employed as the cleaning and polishing component of prophylatic paste compositions. However, in order that the desired optimal level of cleaning and polishing effectiveness be obtained, a different particle size and surface configuration for the substance is needed. For example, a suitable zirconium silicate preparation for use in a dentifrice preparation is disclosed and claimed in U.S. Pat. No. 3,450,813, and suitable zirconium silicate cleaning and polishing agents for use in a prophylactic paste composition are described and claimed in U.S. Pat. Nos. 3,257,282, and 3,330,732.

Prophylactic paste compositions in accordance with the present invention contain from about 0.007 to about 35.7 and preferably about 0.07 – 3.6 of maloaluminate complexes calculated as the maloaluminate anion. The cleaning and polishing agent serves as a carrier and is employed with a range of about 20 to 80%, by weight, depending on the particular formulation as is well known to one skilled in the art.

the prophylactic paste compositions are prepared in a conventional manner and usually include additional ingredients that render the overall composition commercially acceptable. For example, prophylactic paste compositions typically embody conventional components such as bleaching agents, binders, humectants, flavoring agents and the like. A preferred prophylactic paste composition produced in accordance with the present invention is given hereinafter as Example IX.

EXAMPLE IX

| Constituent | Parts by Weight |
|---|---|
| Maloaluminate complex | 10.0 |
| Zirconium silicate | 50.0 |
| Binders | 2.0 |
| Humectants | 20.0 |
| Sweeteners, flavorings, etc. | 2.0 |
| Water | 16.0 |
| | 100.0 |

OTHER ORAL COMPOSITIONS

In addition to dentifrices and prophylactic pastes, the present invention may be used in conjunction with other compositions (e.g., topical solutions and mouthwashes) comprising maloaluminate complexes in the range of about 0.007 – 35.7%, preferably about 0.07 – 3.6%, calculated as maloaluminate anion as shown in the following Examples.

EXAMPLE X - TOPICAL SOLUTION

| Constituent | Parts by Weight |
|---|---|
| Maloaluminate complex (Example I) | 7.55 |
| Water | 91.80 |
| Nonionic surfactant | 0.50 |
| Flavoring, sweetening | 0.05 |
| | 100.00 |

EXAMPLE XI - MOUTHWASH PREPARATION

| Constituent | Parts by Weight |
|---|---|
| Aluminum chloride | 0.90 |
| Sodium malate | 0.66 |
| Water | 71.27 |
| Sodium hydroxide | 0.35 |
| Sorbitol | 8.00 |
| Glycerine | 5.00 |
| Ethanol (95%) | 12.00 |
| Flavorings, colorings, etc. | 0.22 |
| Non-ionic Surfactant | 1.60 |
| | 100.00 |

EXPERIMENTAL EVALUATIONS

The significant articariogenic benefits of the maloaluminate complex-containing oral compositions of this invention have been demonstrated in dental caries studies performed with rats, standard experimental animals for evaluating the effectiveness of anticariogenic agents. A total of 156 weanling (28-day old) Wistar strain rats were randomly divided into 8 equal groups according to sex, body weight, and litter mates. The parents of the weanlings were placed on a low fluoride corn diet and fluoride-free redistilled drinking water one week prior to mating. The mother rats were maintained on this same regimen during their 21-day gestation period and the subsequent 28-day weaning period following the birth of the pups. This procedure eliminates exposure of the pups to any exogenous sources of fluoride during their development.

After weaning, the 28-day old rats were placed on a low fluoride stock corn dental caries inducing diet and fluoride-free redistilled water ad libitum. Once daily 5 days per week the right and left mandibular molars were each swabbed for one minute with the respective topical treatment solution. A cotton swab was used to apply the solution to the molars by freshly dipping into the solution every 15 seconds during the 1-minute treatment. The topical solutions used for treatment were as follows:

| | | pH |
|---|---|---|
| Group 1 | 200 ppm $Al^{+3}$ (as $AlCl_3 . 6H_2O$) + 0.1% acetic acid | Adjusted to 4.1 ± 0.1 |
| Group 2 | 200 ppm $Al^{+3}$ (as $AlCl_3 . 6H_2O$) + 0.38% lactic acid | Adjusted to 7.9 ± 0.1 |
| Group 3 | 200 ppm $Al^{+3}$ (as $AlCl_3 . 6H_2O$)+250 ppm $F-$ (as NaF)+0.1% malic acid | Adjusted to 4.1 ± 0.1 |
| Group 4 | 200 ppm $Al^{+3}$ (as $AlCl_3 . 6H_2O$)+250 ppm $F-$ (as NaF)+0.1% malic acid | Adjusted to 7.9 ± 0.1 |
| Group 5 | 250 ppm $F-$ (as $SnF_2$) | Adjusted to pH 4.1 |
| Group 6 | Fluoride-free redistilled water (control) | Natural |
| Group 7 | Fluoride-free redistilled water (control) | Natural |
| Group 8 | 200 ppm $Al^{+3}$ (as $AlCl_3 . 6H_2O$)+0.1% malic acid | Adjusted to 7.9 ± 0.1 |

The pH of all solutions was adjusted using a concentrated NaOH solution. All solutions were prepared 3 days prior to initiation of the study except the SnF$_2$ treatment solution which must be prepared fresh daily. These original stock solutions were used throughout the entire study, except for the 200 ppm Al$^{+3}$ + 0.38% lactic acid solution which was prepared fresh once a week due to instability.

The rats were housed in an air-conditioned room in cages with raised screen floors, and the usual sanitary measures in the care of laboratory animals were strictly followed. The lights were time regulated to insure 12 hours of light and 12 hours of darkness.

The weight of the rats was determined initially, and then at one-month periods until the conclusion of the study. The control animals in Group 7 were periodically sacrificed during the study to determine when the carious process had reached the proper stage for analysis. For this animal study it was necessary to continue the study for 11 weeks in order for an adequate degree of dental caries to have developed. After the 11-week period the animals were sacrificed by chloroform inhalation. The mandibles were removed and placed in 10% formalin for two days, then stored in 70% ethanol until the time of examination. All animals were coded in order to prevent identification of the treatment groups by the examiners. The teeth were dried with air, and the incidence and severity of the dental caries determined using a binocular dissecting microscope at 20X magnification. Dental caries were determined with the aid of a sharp dental explorer and tabulated accurately on an examination form according to location and size of the lesion. Briefly, the method of scoring for dental caries was as follows: each fissure cavity was counted as one lesion according to its location (incidence) — the first, second, and third molars have, respectively, three, two and one fissures (use of the stock corn diet induces only fissure caries). The size (severity) of the lesions was determined by arbitrarily classifying them as 1, 2, or 3, where 1 is the smallest that can be detected; 2 shows deep penetration into the dentin; and 3 is a destruction of the fissure or cusp with complete cavitation in the pulp chamber. All the teeth were independently examined and classified blindly by two different examiners.

Dental caries data are given in the Table. In order to verify the results obtained in the foregoing study, the entire study was repeated, and the data from the replicate are also reported in the Table. The data from the two studies are also presented in combined form in the Table.

Numerically all experimental groups demonstrated a reduction in dental caries. However, the results from both studies for aluminum plus acetic acid (Group 1) and the aluminum plus lactic acid (Group 2) were not statistically significant from the controls, but the results were significant for Groups 3 and 4 (aluminum and malic acid with fluoride at acidic and alkaline pH, respectively) and for Group 5 (stannous fluoride). Only Group 8 (maloaluminate complex) of the non-fluoride groups produced significant reductions. While the results achieved with the maloaluminate complexes of this invention were not statistically significantly different from the reductions obtained with stannous fluoride, they nontheless demonstrate that significant dental caries reduction can be achieved without fluoride, employing the maloaluminate complexes in oral preparations at a pH in the slightly alkaline region.

TABLE

| Group No. | Treatment Solution | Adjusted pH | STUDY #1 | | | STUDY #2 | | | Combined Data | | |
|---|---|---|---|---|---|---|---|---|---|---|---|
| | | | No. of Rats | Caries Incidence | % Reduction | No. of Rats | Caries Incidence | % Reduction | No. of Rats | Caries Incidence | % Reduction |
| 1 | 200 ppm Al+3 + 0.1% acetic acid | 4.1 | 20 | 4.85±1.92 | 18.5% | 19 | 3.95±2.32 | 30.1% | 39 | 4.41±2.14 | 24.0% |
| 2 | 200 ppm Al+3 + 0.38% lactic acid | 7.9 | 19 | 5.26±1.69 | 11.7 | 19 | 4.37±1.46 | 22.7 | 38 | 4.82±1.62 | 16.9 |
| 3 | 200 ppm Al+3 + 250 ppm F−(NaF) + 0.1% ppm malic acid | 4.1 | 18 | 4.00±1.49 | 32.9 | 20 | 3.20±2.58 | 43.4 | 38 | 3.58±2.15 | 38.3 |
| 4 | 200 ppm Al+3 + 250 ppm F−(NaF) + 0.1% malic acid | 7.9 | 19 | 4.32±1.52 | 27.5 | 20 | 4.05±2.16 | 28.3 | 39 | 4.18±1.86 | 27.9 |
| 5 | 250 ppm F−(SnF$_2$) | 4.1 | 20 | 4.25±2.04 | 28.7 | 19 | 3.57±2.24 | 36.8 | 39 | 3.92±2.14 | 32.4 |
| 6&7 | Fluoride free water | Natural | 25 | 5.96±1.39 | — | 26 | 5.65±2.36 | — | 51 | 5.80±1.93 | — |
| 8 | 200 ppm Al+3 + 0.1% malic acid | 7.9 | 16 | 3.37±2.06 | 43.5 | 17 | 3.94±1.81 | 30.3 | 33 | 3.67±1.93 | 36.7 |

We claim:

1. Aqueous anionic maloaluminate complexes of the structure:

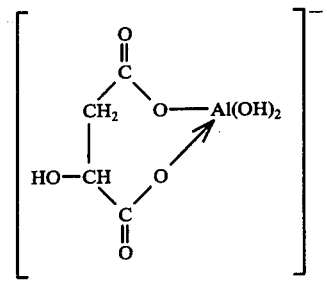

2. Oral compositions for dental caries prophylaxis comprising:

an anticariogenically effective and non-toxic amount of an aqueous anionic maloaluminate complex of the structure:

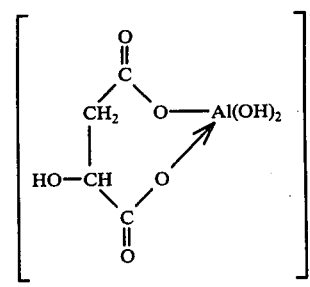

and a carrier suitable for use in the oral cavity, the pH of such composition lying in the range of about 7.0 – 9.0.

3. An oral composition, as claimed in claim 2, wherein the carrier comprises a dental abrasive.

4. An oral composition, as claimed in claim 3, wherein the dental abrasive is purified, calcined kaolin.

5. An oral composition as claimed in claim 2, wherein the carrier comprises water.

6. An oral composition, as claimed in claim 2, wherein the maloaluminate complex is present at a level of about 0.007 – 35.7%, by weight, of the composition, calculated as maloaluminate complex anion.

7. A method for increasing the dental caries resistance of the teeth comprising the application thereto of an oral composition as claimed in claim 3.

8. A method, as claimed in claim 7, wherein the complex anion is present in the composition at a level of about 0.007 – 35.7%, by weight, calculated as maloaluminate complex anion.

* * * * *

UNITED STATES PATENT AND TRADEMARK OFFICE
CERTIFICATE OF CORRECTION

PATENT NO. : 4,042,680
DATED : August 16, 1977
INVENTOR(S) : Joseph C. Muhler, et al.

It is certified that error appears in the above—identified patent and that said Letters Patent are hereby corrected as shown below:

Page 1 in item [22] of the heading of the patent, the filing date should read "Aug. 2, 1976" instead of "Aug. 2, 1975."

Signed and Sealed this

Twenty-ninth Day of November 1977

[SEAL]

Attest:

RUTH C. MASON
Attesting Officer

LUTRELLE F. PARKER
Acting Commissioner of Patents and Trademarks